US012594543B2

(12) United States Patent
Wang et al.

(10) Patent No.: US 12,594,543 B2
(45) Date of Patent: Apr. 7, 2026

(54) METHOD FOR ACETYLENE HYDROCHLORINATION TO VINYL CHLORIDE CATALYZED BY ULTRA-LOW CONTENT AURUM-BASED MATERIAL

(71) Applicants: Nanjing Tech University, Nanjing (CN); CNSIG JILANTAI CHLOR-ALKALI CHEMICAL CO., LTD., Inner Mongolia (CN)

(72) Inventors: Chuan Wang, Nanjing (CN); Guangbin Wang, Inner Mongolia (CN); Lanxin Ye, Nanjing (CN); Jie Zhou, Inner Mongolia (CN); Heng Wang, Nanjing (CN); Ming Xu, Inner Mongolia (CN); Wensai Zhu, Nanjing (CN); Guoqing Guo, Inner Mongolia (CN); Hongxia Liu, Nanjing (CN); Hongda Li, Inner Mongolia (CN); Wei Su, Inner Mongolia (CN); Miao Chen, Inner Mongolia (CN)

(73) Assignees: Nanjing Tech University, Nanjing (CN); CNSIG JILANTAI CHLOR-ALKALI CHEMICAL CO., LTD., Inner Mongolia (CN)

( * ) Notice: Subject to any disclaimer, the term of this patent is extended or adjusted under 35 U.S.C. 154(b) by 456 days.

(21) Appl. No.: 18/318,995

(22) Filed: May 17, 2023

(65) Prior Publication Data

US 2023/0381747 A1    Nov. 30, 2023

(30) Foreign Application Priority Data

May 25, 2022    (CN) .......................... 202210577176.8

(51) Int. Cl.
*B01J 21/18* (2006.01)
*B01J 23/52* (2006.01)
(Continued)

(52) U.S. Cl.
CPC ............... *B01J 23/52* (2013.01); *B01J 21/18* (2013.01); *B01J 27/24* (2013.01); *B01J 37/0036* (2013.01);
(Continued)

(58) Field of Classification Search
CPC ........ B01J 21/18; B01J 23/52; B01J 37/0036; B01J 37/0201; B01J 37/0203;
(Continued)

(56) References Cited

U.S. PATENT DOCUMENTS

2010/0197956 A1*   8/2010   Hagemeyer .......... B01J 37/0201
                                                        560/208

FOREIGN PATENT DOCUMENTS

CN        102921473 A   *   2/2013
CN        103381369 A   *   11/2013
(Continued)

OTHER PUBLICATIONS

Machine translation of Wang et al (CN114890864A), publication date Aug. 12, 2022.*
(Continued)

*Primary Examiner* — Jun Li

(74) *Attorney, Agent, or Firm* — MUNCY, GEISSLER, OLDS & LOWE, P.C.

(57) ABSTRACT

In a method for acetylene hydrochlorination to vinyl chloride catalyzed by ultra-low content aurum-based material, a nitrogen-modified activated carbon support is obtained by using 1,10-phenanthroline as a modifier. A trace amount of aurum is used as a main active component and an organic solvent with a low polarity and a low boiling point, isopropanol, is used as a solvent. An ultra-low content of aurum-based catalyst with the aurum loading amount of 0.01 wt % using the above nitrogen-modified activated carbon as a support is prepared by improving the synthesis procedure,
(Continued)

and the efficiency of the catalyst is significantly improved. The catalyst has high activity and vinyl chloride selectivity for acetylene hydrochlorination to vinyl chloride, which is low cost, no mercury pollution, simple in preparation process and expansibility, and has great industrial application value.

6 Claims, 2 Drawing Sheets

(51) Int. Cl.

| | |
|---|---|
| *B01J 27/24* | (2006.01) |
| *B01J 37/00* | (2006.01) |
| *B01J 37/02* | (2006.01) |
| *B01J 37/08* | (2006.01) |
| *C07C 17/08* | (2006.01) |

(52) U.S. Cl.
CPC ........... *B01J 37/0205* (2013.01); *B01J 37/08* (2013.01); *C07C 17/08* (2013.01)

(58) Field of Classification Search
CPC .... B01J 37/0207; B01J 37/0213; B01J 37/08; B01J 37/082; C07C 21/06
See application file for complete search history.

(56) References Cited

FOREIGN PATENT DOCUMENTS

| | | | | | |
|---|---|---|---|---|---|
| CN | 111420694 | A | * | 7/2020 | ............. C07C 17/08 |
| CN | 111454119 | A | * | 7/2020 | ............. B01J 27/24 |
| CN | 112387275 | A | * | 2/2021 | ............. B01J 31/26 |
| CN | 113578318 | A | * | 11/2021 | ............. B01J 23/52 |
| CN | 113634280 | A | * | 11/2021 | .......... B01J 31/2404 |
| CN | 114890864 | A | * | 8/2022 | .......... B01J 37/0213 |

OTHER PUBLICATIONS

He et al. (Highly Active AuCu-Based Catalysts for Acetylene Hydrochlorination Prepared Using Organic Aqua Regia, Materials 2019, 12, 1310; doi:10.3390/ma12081310).*

* cited by examiner

METHOD FOR ACETYLENE HYDROCHLORINATION TO VINYL CHLORIDE CATALYZED BY ULTRA-LOW CONTENT AURUM-BASED MATERIAL

CROSS REFERENCE TO RELATED APPLICATIONS

The present application claims priority to Chinese Patent Application No. CN 202210577176.8, which was filed on May 25, 2022, the entire contents of which are hereby incorporated by reference.

TECHNICAL FIELD

The present invention belongs to the field of catalyst preparation technology and application, and particularly relates to a method for preparing an ultra-low content aurum-based catalyst for acetylene hydrochlorination to vinyl chloride and application thereof.

BACKGROUND ART

Polyvinyl chloride (PVC) is one of the world's five major engineering plastics (PVC, PE, PP, PS, and ABS), accounting for more than 16% of the total plastic demand, and is one of the most widely used thermoplastics in the healthcare and medical equipment, electronics and automotive industries. In addition, it is also commonly used in building and construction due to its physical properties and chemical resistance. PVC's global total consumption is estimated to exceed 40 million tons in 2021 and is expected to rise to 56.2 million tons in 2026.

Polyvinyl chloride (PVC) is obtained by radical polymerization of vinyl chloride (VCM) monomer. About 90% of VCM production is used to produce PVC. Increasing PVC capacity requires increasing VCM capacity. The current methods of VCM production include acetylene hydrochlorination method, ethylene oxychlorination method, and ethane oxychloride method. Acetylene hydrochlorination has the advantage of a one-step reaction, while the vinyl process has multiple reactions, which reduces the product yield and complicates the separation step. Acetylene hydrochlorination is one of the most important synthetic routes in VCM production due to the special lean oil and coal-rich energy structure in China. In the traditional industrial acetylene method, the catalyst system uses activated carbon as a support and $HgCl_2$ as an active center. Due to the toxicity and volatility of $HgCl_2$, which poses a serious threat to environmental safety and human health, the United Nations Environment Programme adopted the Minamata Convention on Mercury in 2013, which aims to limit the use of mercury. Under the double constraints of mercury resource depletion and environmental protection policy, developing a new, green, and efficient mercury-free catalyst is the key to realize the green sustainable development of the polyvinyl chloride industry in China.

Mercury-free catalysts can be divided into two types: metal-free catalysts and supported metal catalysts. Among many supported metal catalysts, noble metal catalysts are considered as promising catalysts for industrial of their high activity and stability. The pioneering work by Hutchings etc. investigated the use of supported metal catalysts in acetylene hydrochlorination. Several metal chlorides including $Au^{3+}$, $Pt^{4+}$, $Pd^{2+}$, $Ru^{3+}$, and $Bi^{3+}$ were used as non-mercury catalysts for acetylene hydrochlorination, and $AuCl_3$ is considered the best catalyst to replace $HgCl_2$ due to its higher activity. Since then, aurum-based catalysts have been widely concerned by researchers and become an important research direction in the development of mercury-free catalysts for acetylene hydrochlorination.

At present, most of the mercury-free catalysts are supported on activated carbon (AC), mainly due to the advanced pore structure, large specific surface area, and good adsorption performance of the activated carbon, but its hydrophilicity is poor and surface activity is low, in the reaction it is easy to crush, easy to coke, and not easy to regenerate. The introduction of nitrogen atoms into the carbon skeleton (nitrogen-containing carbon materials) can not only improve the hydrophilicity and surface activity of traditional activated carbon, but also provide lone pair electrons, improve its surface polarity and electron transport properties, effectively modulate the physical and chemical properties of activated carbon, and thus enhance the reactivity. Nowadays, the research on the application of nitrogen-containing carbon materials with excellent performance as catalyst support in acetylene hydrochlorination has become a hot spot in the clean production of vinyl chloride in the chlor-alkali industry.

Patent CN202110227232.0 invented a uracil-modified low-content aurum-based catalyst (aurum loading at 0.1 wt %). Under the conditions of reaction temperature 150° C., $GHSV(C_2H_2)=522$ $h^{-1}$ and the raw gas ratio $V_{(HCl)}/V_{(C2H2)}=1.15$, the conversion reached 54%; the vinyl chloride selectivity reached 99.23%. The low aurum loading of the invention patent effectively saves cost, but the acetylene conversion is slightly lower.

Patent CN201410255462.8 discloses a catalyst using activated carbon as a support, cysteine, cystine, methionine, and thiourea as organic surface modifiers of the activated carbon, and aurum trichloride as an active center (aurum loading is 0.325 wt %). The catalyst was prepared by several steps, such as the washing of activated carbon, preparation of modifier solution, modification of activated carbon, washing of modified support, preparation of Au solution, and catalyst loading. Under the conditions of reaction temperature 180° C., $GHSV(C_2H_2)=200$ $h^{-1}$, the raw gas ratio $V_{(HCl)}/V_{(C2H2)}=1.2$, and acetylene conversion can reach 98% with 10 mL of catalyst. This invention patent has good catalytic activity and stability in acetylene hydrochlorination, but the preparation process is too complicated with high aurum loading and high hydrogen chloride acetylene feeding.

Patent CN202011441893.5 invented a catalyst using activated carbon pretreated by microwave irradiation nitrogen modification technology as a support, aurum as a catalytically active component (aurum loading at 0.125 wt %), and potassium or sodium compounds as a cocatalyst component (loading at 2.5 wt %). Under the conditions of reaction temperature 180° C., $GHSV(C_2H_2)=250$ $h^{-1}$, the raw gas ratio $V_{(HCl)}/V_{(C2H2)}=1.1$, the acetylene conversion can reach 73% by using the catalyst; the vinyl chloride selectivity reached 99.88%. The lower aurum loading of the invention patent effectively saves catalyst preparation costs, but the acetylene hourly space velocity is lower.

In conclusion, aurum-based catalysts are still promising catalysts for industrial applications, but most of the current aurum-based catalysts have the disadvantages of complicated synthesis steps, high synthesis cost, and low acetylene conversion at high acetylene hourly space velocity. In addition, Au was easily reduced to $Au^0$ during acetylene hydrochlorination, which resulted in catalyst deactivation. The presence of nitrogen species was beneficial to change the electronic environment around the activated carbon to stabilize the active center, improve the catalytic activity and reduce the deactivation rate. Therefore, in ensuring high catalytic activity, it is very important to find a low-cost, simple, and easy-to-expand synthesis method, which provides a better basis for the industrial production of catalysts and subsequent catalyst modification.

SUMMARY OF THE INVENTION

The technical problem to be solved by the present invention is: to provide a method for acetylene hydrochlorination to vinyl chloride catalyzed by ultra-low content aurum-based material. The innovation of this method is that a catalyst with ultra-low aurum content, high activity, and good stability was prepared by using the incipient wetness impregnation method, through nitrogen modification of activated carbon support, with 1,10-phenanthroline as a modifier, adjusting the best ratio of solvent and support and optimizing the synthesis procedure to greatly reduce the Au loading to 0.01 wt %. Under the conditions of GHSV $(C_2H_2)= 170 \text{ h}^{-1}$, $V_{(C2H2)}/V_{(HCl)}=1:1.05$ and reaction temperature of 180° C., the acetylene conversion can reach 58.8%, the vinyl chloride selectivity is greater than 99%, which provides a unique and effective solution for the industrial production of vinyl chloride at low cost and high efficiency.

In order to solve the technical problem of the present invention, the technical solution proposed is a method for acetylene hydrochlorination to vinyl chloride catalyzed by ultra-low content aurum-based material, characterized in that:

The ultra-low content aurum-based catalyst was used in acetylene hydrochlorination to vinyl chloride. And under the conditions of GHSV$(C_2H_2)$=170 $\text{h}^{-1}$, $V_{(C2H2)}/V_{(HCl)}$=1:1.05 and reaction temperature of 180° C., vinyl chloride was produced. The reaction route was as follows:

$$C_2H_2+HCl \rightarrow C_2H_3Cl$$

wherein the method for preparing an ultra-low content aurum-based catalyst for acetylene hydrochlorination to vinyl chloride comprises the following steps of:

(1) preparing a precursor solution: dissolving 0.1082 g of chloroauric acid ($HAuCl_4·4H_2O$ solids with Au≥47.5%) in an organic solvent, isopropanol (IPA), and preparing the IPA solution of $HAuCl_4·4H_2O$ by shaking and ultrasonic treatment; adjusting the ratio of isopropanol to chloroauric acid to prepare the IPA solution of $HAuCl_4·4H_2O$ as 0.2164 mg $HAuCl_4·4H_2O$/100 uL IPA;

(2) preparing a nitrogen-modified carbon support: weighing 3 g of activated carbon into a beaker containing 25 mL of deionized water, and adding 1.5 mL of glacial acetic acid under stirring at room temperature for 30 min; weighing 25 mL of deionized water, 1.0 g of nitrogen source 1,10-phenanthroline and 1.5 mL of 30% hydrogen peroxide, successively adding into the above beaker, and continue stirring at room temperature in the dark for 24 h; The mixture was filtered and dried in an oven at 90° C. for 12-24 h; Under a nitrogen flow rate of 50 mL/min and a heating rate of 5° C./min in a tube furnace, increasing the calcination temperature to 900° C. and keeping for 1 h to obtain a nitrogen-modified carbon support;

(3) preparing the catalyst by an impregnation method: taking 2999.7 mg of the nitrogen-modified carbon support prepared in step (2), and laying it in a mortar; taking 292 uL of the $HAuCl_4·4H_2O$ solution prepared in step (1), adding isopropanol to prepare a 6 mL solution, and then uniformly dropwise adding it onto the above nitrogen-modified carbon support to finally obtain nitrogen-modified carbon support/g:solution/ mL=0.5; the catalyst was thoroughly ground in the clockwise direction to have a smooth surface, and the mass ratio of the aurum to the support is (4) drying the ground catalyst in a blast drying oven for 12-24 h.

Preferably, isopropanol with low polarity and low boiling point is used as a solvent, 0.1082 g of chloroauric acid ($HAuCl_4·4H_2O$ solids with Au≥47.5%) are dissolved in 50 mL of isopropanol at room temperature, shaken with a homogenizer for 10 min, and then sonicated for 30 min to prepare an isopropanol solution of $HAuCl_4·4H_2O$, 0.2164 mg $HAuCl_4·4H_2O$/100 uL IPA, and stored in a sealed dark state at low temperature.

Preferably, the Au mass content in chloroauric acid in step (1) is Au≥47.5%, and the ultrasonic frequency in step (1) is 40 KHz.

Preferably, the activated carbon in step (2) is non-pretreated 200 mesh activated carbon.

Preferably, the theoretical nitrogen loading in step (2) is 3.9 wt %.

Preferably, the aurum-based catalyst prepared in step (3) has a mass ratio of aurum: support of 0.01:99.99.

Preferably, the ground catalyst in step (3) should have a smooth surface and then be dried in a blast drying oven at 90° C.

Preferably, the specific steps are as follows:

(1) loading catalyst: padding a layer of quartz wool with a thickness of 10 mm on the middle position of a quartz reaction tube with a diameter of 10 mm, adding the catalyst into the reaction tube and ensuring that the catalyst is smooth, and then padding a layer of quartz wool with a thickness of 10 mm to cover the catalyst;

(2) before reaction: purging the whole pipeline with $N_2$ at a flow rate of 20 mL min$^{-1}$ for 60 min, so as to remove air and moisture in the system; at the same time, increasing the temperature by 5° C./min to 150° C. and keeping for 30 min, and then increasing the temperature by 5° C./min to 180° C.; after that, introducing hydrogen chloride at a flow rate of 20 mL/min and keeping for 30 min, subsequently introducing both reaction gas at a flow rate of $V_{C2H2}$=16 mL/min and $V_{HCl}$=16.8 mL/min and keeping for 10 min, so as to ensure that the catalyst is in a gas atmosphere of acetylene and hydrogen chloride; then reducing the flow rate of the reaction gas at a ratio of $V_{C2H2}/V_{HCl}$=1: 1.05, and starting to detect after keeping for 10 min at the reaction flow rate;

(3) after reaction: first passing the gas phase product through an absorption flask containing NaOH solution to remove excess HCl and then analyzing online by gas chromatography GC-9790II to evaluate acetylene conversion and VCM selectivity.

The advantageous effects of the present invention are as follows:

The present invention provides a method for preparing an ultra-low content aurum-based catalyst, which greatly reduces preparation costs, is simpler to operate, and is scalable compared to other methods. The technical solution adopted by the present invention to solve the technical problem is: by using 1,10-phenanthroline as the activated carbon organic surface modifier to modify the support, selecting the appropriate low-polarity low-boiling point organic solvent and determining the ratio between the solvent and the catalyst, while greatly reducing the content of Au in the catalyst, the ultra-low content Au-based catalyst with nitrogen-modified carbon as the support was prepared, with the aurum loading of 0.01 wt %. Production costs are effectively saved; the catalyst prepared by the present invention has excellent catalytic performance for acetylene hydrochlorination and is suitable for industrial production.

(1) The catalyst with aurum as the main active component was supported on nitrogen-modified activated carbon by using isopropanol as the solvent. Isopropanol is a typical low-boiling, low-polarity organic solvent that is miscible with water as well as a variety of organic solvents and has low industrial production costs. The low-polarity organic solvent can wet the hydrophobic activated carbon better, make the active component more quickly and evenly distributed on the surface of the support, effectively improve the dispersion of Au, ease the aggregation of the active component, and then improve the catalytic efficiency of the active component. By rationally controlling the optimal ratio of nitrogen-modified carbon support to solvent:support/g: solution/mL=0.5, the efficiency of the catalyst has been effectively improved.

(2) The support used in the present invention: comparing the effect of one or more of EDTA, 1,10-phenanthroline, 2-methylimidazole, quinoline, vitamin B1, TCCA, and melamine as a nitrogen source to modify activated carbon, 1,10-phenanthroline was selected as nitrogen source modifier. Under the same conditions, nitrogen-modified carbon support can stabilize the active center, improve the catalytic activity and reduce the deactivation rate by changing the electronic environment of activated carbon. Compared to prior methods: firstly, the modifier selected in the present invention is non-toxic and harmless, and inexpensive; secondly, the modifier of the present invention is used in a small amount and has a high loading rate, thus being lower in modification cost compared to other technologies; in addition, the nitrogen modification process of the present invention is simple in operation, environmentally friendly and reduces energy consumption. In summary, the process of the present invention significantly improves the catalytic activity and stability of the catalyst by improving the support nitrogen modification process. Compared with unmodified activated carbon, the nitrogen-modified carbon in the present technology can bring the catalyst excellent catalytic activity and can be used industrially.

(3) Keeping a nitrogen flow rate of 50 mL/min in step (2) of the present invention, calcining is carried out at a temperature rise rate of 5° C./min to 900° C. and keeped for 1 h to obtain a nitrogen-modified carbon support, which has better performance than the catalyst calcined at 650° C.

(4) In step (3) of the present invention, the catalyst was ground to be smooth in a clockwise direction within 10 min, and then dried at 90° C. in a blast drying oven. Grinding to smoothness in a short time can reduce the contact of the catalyst with air at normal temperature and improve the loading rate and dispersion of the active component.

6

Figure 1:
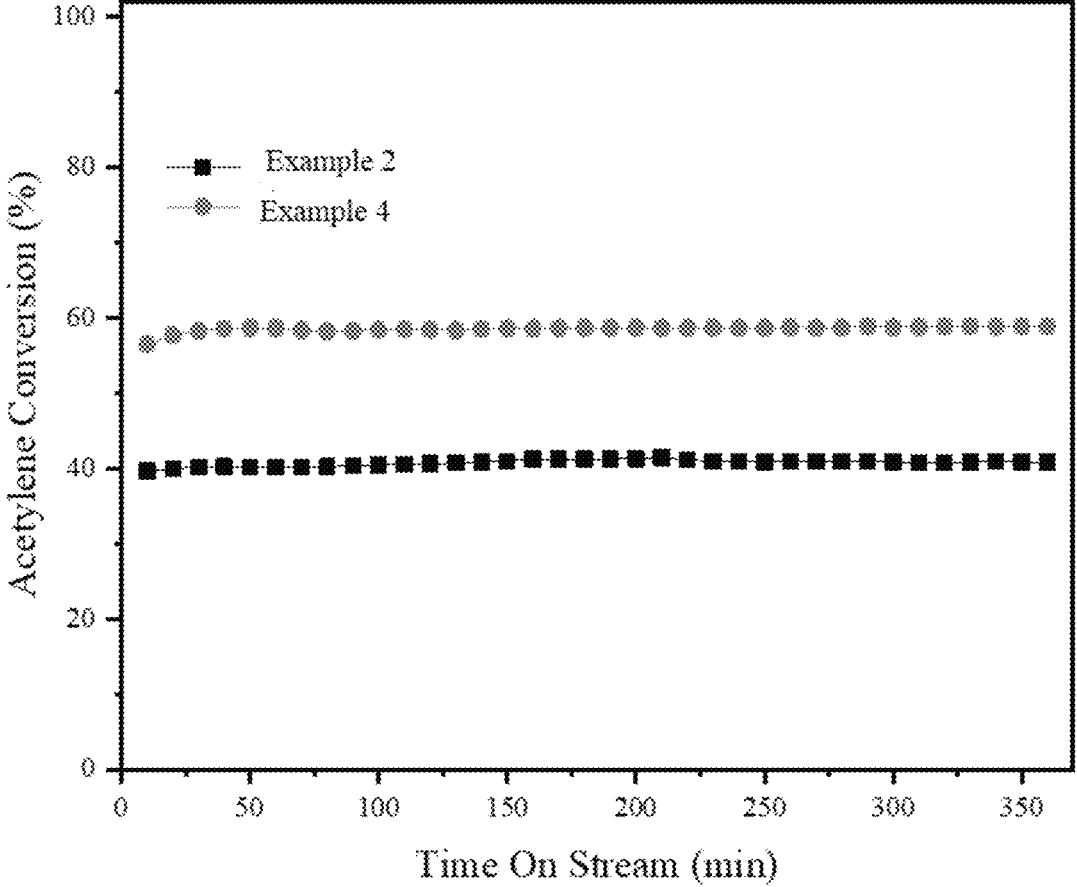
FIG. 1 acetylene conversion using catalysts of Examples 2 and 4 in acetylene hydrochlorination
Figure 2:
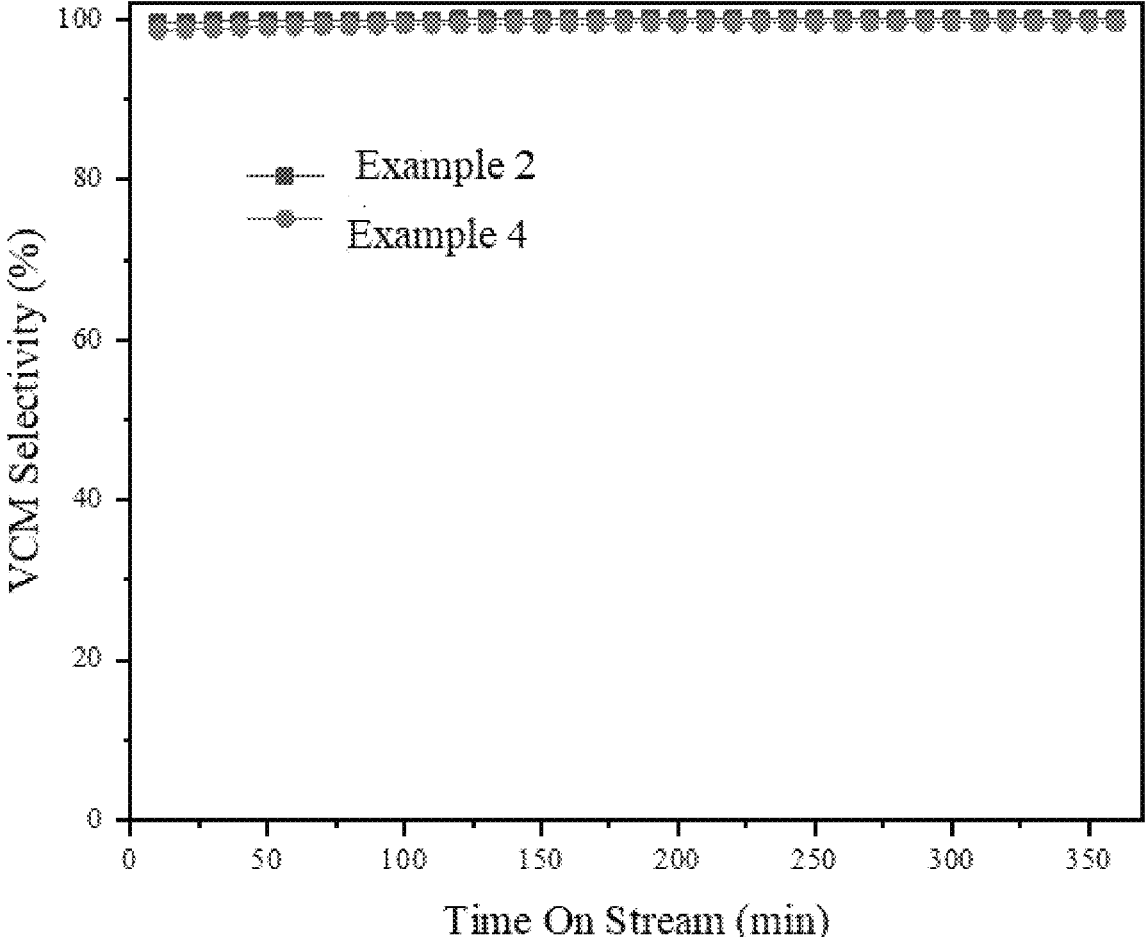

FIG. 2 vinyl chloride selectivity using catalysts of Examples 2 and 4 in acetylene hydrochlorination

DETAILED DESCRIPTION OF THE INVENTION

Example 1 Catalyst Preparation 2997 mg of 200 mesh activated carbon (AC*) was weighed and spread in a mortar. 2920 uL of prepared IPA solution of $HAuCl_4 \cdot 4H_2O$ (0.2164 mg $HAuCl_4 \cdot 4H_2O/100$ uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of $HAuCl_4 \cdot 4H_2O$ was added dropwise and uniformly to the above activated carbon, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.1% Au/AC* (IPA).

Comparative Example 1-1 Catalyst Preparation

Preparing precursor solution: 0.1082 g of chloroauric acid ($HAuCl_4 \cdot 4H_2O$ solids with Au≥47.5%) was dissolved in deionized water with high polarity and high boiling point and prepared the aqueous solution of $HAuCl_4 \cdot 4H_2O$ by shaking and ultrasonic treatment.

2997 mg of 200 mesh activated carbon (AC*) was weighed and spread in a mortar. 2920 uL of prepared aqueous solution of $HAuCl_4 \cdot 4H_2O$ (0.2164 mg $HAuCl_4 \cdot 4H_2O/100$ uL $H_2O$) was taken, and added into deionized water to prepare 6 mL solution, shaken for 10 min, and then sonicated at room temperature for 30 min with an ultrasonic frequency of 40 KHz to rapidly dissolve and mix it; Then, the resulted aquesous solution of $HAuCl_4 \cdot 4H_2O$ was added dropwise and uniformly to the activated carbon, which is rapidly ground in a clockwise direction after the addition until the catalyst surface is smooth. It was then transferred to a watch glass and dried in a blast drying oven at 100° C. for 12 h. At the end of drying, it is sealed and stored.

The catalyst was designated 0.1% Au/AC* ($H_2O$).

Example 2 Catalyst Preparation 2999.3 mg of 200 mesh activated carbon (AC*) was weighed and spread in a mortar. 292 uL of prepared IPA solution of $HAuCl_4 \cdot 4H_2O$ (0.2164 mg $HAuCl_4 \cdot 4H_2O/100$ uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of $HAuCl_4 \cdot 4H_2O$ was added dropwise and uniformly to the activated carbon, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% Au/AC* (IPA).

Example 3 Catalyst Preparation 3 g of 200 mesh activated carbon (AC*) was weighed and placed into a beaker containing 25 mL of deionized water, and 1.5 mL of glacial acetic acid was added under stirring at room temperature for 30 min; 25 mL of deionized water, 1.8 g of EDTA and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; $N_1AC^*$ was obtained by calcining the dried solid in a tube furnace at a heating rate of to 900° C. and keeping for 1 h under a nitrogen flow rate of 25-50 mL/min. The theoretical nitrogen loading was 3.1%.

2999.3 mg of $N_1AC^*$ was weighed and spread in a mortar. 292 uL of prepared IPA solution of $HAuCl_4\cdot4H_2O$ (0.2164 mg $HAuCl_4\cdot4H_2O$/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of $HAuCl_4\cdot4H_2O$ was added dropwise and uniformly to the above $N_1AC^*$, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% $Au/N_1AC^*$ (IPA).

Example 4 Catalyst Preparation 3 g of 200 mesh activated carbon (AC*) was weighed and placed into a beaker containing 25 mL of deionized water, and 1.5 mL of glacial acetic acid was added under stirring at room temperature for 30 min; 25 mL of deionized water, 1.0 g of 1,10-phenanthroline and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; $N_2AC^*$ was obtained by calcining the dried solid in a tube furnace at a heating rate of to 900° C. and keeping for 1 h under a nitrogen flow rate of 25-50 mL/min. The theoretical nitrogen loading was 3.9%.

2999.7 mg of $N_2AC^*$ was weighed and spread in a mortar. 292 uL of prepared IPA solution of $HAuCl_4\cdot4H_2O$ (0.2164 mg $HAuCl_4\cdot4H_2O$/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of $HAuCl_4\cdot4H_2O$ was added dropwise and uniformly to the above $N_2AC^*$, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% $Au/N_2AC^*$ (IPA).

Comparative Example 4-1 Catalyst Preparation 3 g of 200 mesh activated carbon (AC*) was weighed and placed into a beaker containing 25 mL of deionized water, and 1.5 mL of glacial acetic acid was added under stirring at room temperature for 30 min; 25 mL of deionized water, 1.0 g of 1,10-phenanthroline and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; $N_2AC^*$ was obtained by calcining the dried solid in a tube furnace at a heating rate of to 650° C. and keeping for 1 h under a nitrogen flow rate of 25-50 mL/min. The theoretical nitrogen loading was 3.9%.

2999.7 mg of $N_2AC^*$ was weighed and spread in a mortar. 292 uL of prepared IPA solution of $HAuCl_4\cdot4H_2O$ (0.2164 mg $HAuCl_4\cdot4H_2O$/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of $HAuCl_4\cdot4H_2O$ was added dropwise and uniformly to the above $N_2AC^*$, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% $Au/N_2AC^*$-650.

Example 5 Catalyst Preparation 3 g of 200 mesh activated carbon (AC*) was weighed and placed into a beaker containing 25 mL of deionized water, and 1.5 mL of glacial acetic acid was added under stirring at room temperature for 30 min; 25 mL of deionized water, 0.46 g of 2-methylimidazole and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; $N_3AC^*$ was obtained by calcining the dried solid in a tube furnace at a heating rate of to 900° C. and keeping for 1 h under a nitrogen flow rate of 25-50 mL/min. The theoretical nitrogen loading was 4.5%.

2999.7 mg of $N_3AC^*$ was weighed and spread in a mortar. 292 uL of prepared IPA solution of $HAuCl_4\cdot4H_2O$ (0.2164 mg $HAuCl_4\cdot4H_2O$/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of $HAuCl_4\cdot4H_2O$ was added dropwise and uniformly to the above $N_3AC^*$, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% $Au/N_3AC^*$ (IPA).

Example 6 Catalyst Preparation 3 g of 200 mesh activated carbon (AC*) was weighed and placed into a beaker containing 25 mL of deionized water, and 1.5 mL of glacial acetic acid was added under stirring at room temperature for 30 min; 25 mL of deionized water, 1.44 g of quinoline and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; $N_4AC^*$ was obtained by calcining the dried solid in a tube furnace at a heating rate of to 900° C. and keeping for 1 h under a nitrogen flow rate of 25-50 mL/min. The theoretical nitrogen loading was 3.5%.

2999.7 mg of $N_4AC^*$ was weighed and spread in a mortar. 292 uL of prepared IPA solution of $HAuCl_4\cdot4H_2O$ (0.2164 mg $HAuCl_4\cdot4H_2O$/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of $HAuCl_4\cdot4H_2O$ was added dropwise and uniformly to the above $N_4AC^*$, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% Au/N$_4$AC* (IPA).

Example 7 Catalyst Preparation 3 g of 200 mesh activated carbon (AC*) was weighed and placed into a beaker containing 25 mL of deionized water, and 1.5 mL of glacial acetic acid was added under stirring at room temperature for 30 min; 25 mL of deionized water, 0.94 g of vitamin B1 and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; N$_5$AC* was obtained by calcining the dried solid in a tube furnace at a heating rate of to 900° C. and keeping for 1 h under a nitrogen flow rate of 25-50 mL/min. The theoretical nitrogen loading was 4.0%.

2999.7 mg of N$_5$AC* was weighed and spread in a mortar. 292 uL of prepared IPA solution of HAuCl$_4$·4H$_2$O (0.2164 mg HAuCl$_4$·4H$_2$O/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of HAuCl$_4$·4H$_2$O was added dropwise and uniformly to the above N$_5$AC*, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% Au/N$_5$AC* (IPA).

Example 8 Catalyst Preparation 3 g of 200 mesh activated carbon (AC*) was weighed and placed into a beaker containing 25 mL of deionized water, and 1.5 mL of glacial acetic acid was added under stirring at room temperature for 30 min; 25 mL of deionized water, 0.86 g of TCCA and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; N$_6$AC* was obtained by calcining the dried solid in a tube furnace at a heating rate of to 900° C. and keeping for 1 h under a nitrogen flow rate of 25-50 mL/min. The theoretical nitrogen loading was 4.0%.

2999.7 mg of N$_6$AC* was weighed and spread in a mortar. 292 uL of prepared IPA solution of HAuCl$_4$·4H$_2$O (0.2164 mg HAuCl$_4$·4H$_2$O/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of HAuCl$_4$·4H$_2$O was added dropwise and uniformly to the above N$_6$AC*, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% Au/N$_6$AC* (IPA).

Example 9 Catalyst Preparation 3 g of 200 mesh activated carbon was weighed and placed into a beaker containing 25 mL of deionized water, and 1.5 mL of glacial acetic acid was added under stirring at room temperature for 30 min; 25 mL of deionized water, 0.24 g of melamine and 1.5 mL of hydrogen peroxide (30%) were weighed, successively added into the above beaker, and continued to stir at room temperature in the dark for 24 h; Then, the mixture was filtered and dried in an oven at 90° C. for 12-24 h; N$_7$AC* was obtained by calcining the dried solid in a tube furnace at a heating rate of 5° C./min to 900° C. and keeping for 1 h under a nitrogen flow rate of 25-50 mL/min. The theoretical nitrogen loading was 4.9%.

2999.7 mg of N$_7$AC* was weighed and spread in a mortar. 292 uL of prepared IPA solution of HAuCl$_4$·4H$_2$O (0.2164 mg HAuCl$_4$·4H$_2$O/100 uL IPA) was taken, and added into isopropanol to prepare 6 mL solution, shaken for 10 min, and then sonicated at room temperature for 30 min with an ultrasonic frequency of 40 KHz to rapidly dissolve and mix it; Then, the resulted IPA solution of HAuCl$_4$·4H$_2$O was added dropwise and uniformly to the above N$_7$AC*, which is rapidly ground in a clockwise direction after the addition until the catalyst surface is smooth. It was then transferred to a watch glass and dried in a blast drying oven at 90° C. for 12 h. At the end of drying, it is sealed and stored.

The catalyst was designated 0.01% Au/N$_7$AC* (IPA).

The evaluation process and conditions for all catalysts were:

(1) loading catalyst: padding a layer of quartz wool with a thickness of 10 mm on the middle position of a quartz reaction tube with a diameter of 10 mm, adding the catalyst into the reaction tube and ensuring that the catalyst is smooth, and then padding a layer of quartz wool with a thickness of 10 mm to cover the catalyst.

(2) before reaction: purging the whole pipeline with N$_2$ at a flow rate of 20 mL min$^{-1}$ for 60 min, so as to remove air and moisture in the system; at the same time, increasing the temperature by 5° C./min to 150° C. and keeping for 30 min, and then increasing the temperature by 5° C./min to 180° C. After that, introducing hydrogen chloride at a flow rate of 20 mL/min and keeping for 30 min, subsequently introducing both reaction gas at a flow rate of V(C$_2$H$_2$)=16 mL/min and V(HCl)=16.8 mL/min and keeping for 10 min, so as to ensure that the catalyst is in a gas atmosphere of acetylene and hydrogen chloride; then reducing the flow rate of the reaction gas at a ratio of V(C$_2$H$_2$)/V (HCl)=1:1.05, and starting to detect after keeping for 10 min at the reaction flow rate.

(3) after reaction: first passing the gas phase product through an absorption flask containing NaOH solution to remove excess HCl and then analyzing online by gas chromatography (GC-9790II) to evaluate acetylene conversion and VCM selectivity.

TABLE 1

| Activity test of catalysts for acetylene hydrochlorination | | | |
| --- | --- | --- | --- |
| Catalyst | Reaction temperature (° C.) | GHSV (h$^{-1}$) | Acetylene conversion in 6 h (%) | Vinyl chloride selectivity (%) |
| 0.1% Au/AC* (IPA) (Example 1) | 180 | 170 | 91.6% | >99.0% |
| 0.1% Au/AC* (H$_2$O) (Comparative Example 1-1) | 180 | 170 | 70.9% | >99.0% |
| 0.01% Au/AC* (IPA) (Example 2) | 180 | 170 | 40.8% | >99.0% |
| 0.01% Au/N$_1$AC* (IPA) (Example 3) | 180 | 170 | 51.0% | >99.0% |

TABLE 1-continued

Activity test of catalysts for acetylene hydrochlorination

| Catalyst | Reaction temperature (° C.) | GHSV (h$^{-1}$) | Acetylene conversion in 6 h (%) | Vinyl chloride selectivity (%) |
|---|---|---|---|---|
| 0.01% Au/N$_2$AC* (IPA) (Example 4) | 180 | 170 | 58.8% | >99.0% |
| 0.01% Au/N$_2$AC*-650 (Comparative Example 4-1) | 180 | 170 | 52.2% | >99.0% |
| 0.01% Au/N$_3$AC* (IPA) (Example 5) | 180 | 170 | 48.9% | >99.0% |
| 0.01% Au/N$_4$AC* (IPA) (Example 6) | 180 | 170 | 55.4% | >99.0% |
| 0.01% Au/N$_5$AC* (IPA) (Example 7) | 180 | 170 | 53.8% | >99.0% |
| 0.01% Au/N$_6$AC* (IPA) (Example 8) | 180 | 170 | 46.8% | >99.0% |
| 0.01% Au/N$_7$AC* (IPA) (Example 9) | 180 | 170 | 54.5% | >99.0% |

The ICP test results for Examples 2 and 4 are shown in Table 2.

TABLE 2

ICP Test Results

| Catalyst | Au content in the catalyst (wt %) |
|---|---|
| 0.01% Au/AC* (IPA) (Example 2) | 0.0096% |
| 0.01% Au/N$_2$AC* (IPA) (Example 4) | 0.0090% |

The elemental analysis test results of Examples 2 and 4 are shown in Table 3.

TABLE 3

Elemental analysis test results

| Catalyst | N (%) | C (%) | H (%) | S (%) |
|---|---|---|---|---|
| 0.01% Au/AC* (IPA) (Example 2) | 0.73% | 83.13% | 1.993% | 0.097% |
| 0.01% Au/N$_2$AC* (IPA) (Example 4) | 3.39% | 87.87% | 2.963% | 0.008% |

As can be seen from Table 1, the catalytic activity of 0.1% Au/AC* (IPA) was better than that of 0.01% Au/AC* (H$_2$O) under the condition of the reaction temperature of 180° C. and GHSV(C$_2$H$_2$)=170 h$^{-1}$. Under the condition of the reaction temperature of 180° C. and GHSV(C$_2$H$_2$)=170 h$^{-1}$, 0.01% Au/AC* (IPA) has an acetylene conversion of 40.8% and a vinyl chloride selectivity higher than 99%. Under the optimal synthesis conditions, 0.01% Au/N$_x$AC* (IPA) was prepared by using nitrogen-modified carbon as support. Under the optimal synthesis conditions, the conversion of acetylene was improved obviously and the selectivity of vinyl chloride was higher than 99%, wherein the catalytic activity of synthesized 0.01% Au/N$_2$AC* (IPA) with 1,10- phenanthroline as nitrogen modifier was the best, and under the condition of the reaction temperature of 180° C. and GHSV(C$_2$H$_2$)=170 h$^{-1}$, the conversion of acetylene was 58.8% and the selectivity of vinyl chloride was higher than 99%, respectively. As can be seen from Example 4 and Comparative Example 4-1, the nitrogen-modified carbon support prepared by calcination at 900° C. had a more significant effect on catalytic performance. Combining the ICP analysis results in Table 2 and the elemental analysis results in Table 3, it can be seen that the catalysts prepared under this synthesis method can maintain high Au and N loadings, indicating that the method of the present invention has significant practical value.

The present invention is not limited to the specific embodiments described in the above embodiments, and all technical solutions formed by equivalent replacement are within the scope of protection required by the present invention.

The invention claimed is:

1. A method for acetylene hydrochlorination to vinyl chloride catalyzed by aurum-based
catalyst comprising using the aurum-based catalyst reacting acetylene and hydrochloride (HCl) under Gas Hourly Space Velocity of C$_2$H$_2$ (acetylene) (GHSV (C$_2$H$_2$)) being 170 h$^{-1}$, volume ratio of acetylene to hydrochloride of V$_{(C2H2)}$/V$_{(HCl)}$=1:1.05, and reaction temperature of 180° C. to obtain vinyl chloride wherein the reaction route is as follows:

$$C_2H_2 + HCl \rightarrow C_2H_3Cl$$

wherein the method further comprises preparing the aurum-based catalyst for acetylene hydrochlorination to vinyl chloride comprises the following steps:
(1) preparing a precursor solution: dissolving 0.1082 g of chloroauric acid (HAuCl$_4$·4H$_2$O solids with Au≥47.5% in the HAuCl$_4$·4H$_2$O solids) in isopropanol (IPA) by shaking and ultrasonic treatment; adjusting a ratio of isopropanol to chloroauric acid to prepare the IPA solution of HAuCl$_4$·4H$_2$O as 0.2164 mg HAuCl$_4$·4H$_2$O/100 μL IPA;
(2) preparing a nitrogen-modified carbon support: weighing 3 g of 200 mesh activated carbon into a beaker containing 25 mL of deionized water, and adding 1.5 mL of glacial acetic acid under stirring at room temperature for 30 min; further adding 25 mL of deionized water, 1.0 g of nitrogen source 1,10-phenanthroline and 1.5 mL of 30% hydrogen peroxide successively into the beaker, and continuing stirring at room temperature in dark for 24 h; filtering and drying the mixture in an oven at 90° C. for 12-24 h; calcinating the filtered and dried mixture under a nitrogen flow rate of 50 mL/min and a heating rate of 5° C./min in a tube furnace, increasing the calcination temperature to 900° C. and keeping for 1 h to obtain a nitrogen-modified carbon support;
(3) preparing the catalyst by an impregnation method: taking 2999.7 mg of the nitrogen-modified carbon support prepared in step (2), and laying it in a mortar; taking 292 μL of the HAuCl$_4$·4H$_2$O solution prepared in step (1), adding isopropanol to 6 mL, and then uniformly dropwise adding it onto the above nitrogen-modified carbon support to finally obtain nitrogen-modified carbon support/g: solution/mL=0.5; the catalyst is thoroughly ground in the clockwise direction to have a smooth surface, and the mass ratio of the aurum to the nitrogen-modified carbon support is 0.01:99.99;

(4) drying the ground catalyst in a blast drying oven for 12-24 h.

2. The method for acetylene hydrochlorination to vinyl chloride catalyzed by aurum-based catalyst of claim 1, further comprising using isopropanol as a solvent, 0.1082 g of chloroauric acid ($HAuCl_4 \cdot 4H_2O$ solids with $Au \geq 47.5\%$) are dissolved in 50 mL of isopropanol at room temperature, shaken with a homogenizer for 10 min, and then sonicated for 30 min to prepare an isopropanol solution of $HAuCl_4 \cdot 4H_2O$, 0.2164 mg $HAuCl_4 \cdot 4H_2O$/100 μL IPA, and stored in a sealed state.

3. The method for acetylene hydrochlorination to vinyl chloride catalyzed by aurum-based catalyst claim 1, wherein the mass content of Au in chloroauric acid in step (1) is $Au \geq 47.5\%$, and the ultrasonic frequency in step (1) is 40 KHz.

4. The method for acetylene hydrochlorination to vinyl chloride catalyzed by aurum-based catalyst of claim 1, wherein the nitrogen loading of 1,10-phenanthroline in step (2) is 3.9%.

5. The method for acetylene hydrochlorination to vinyl chloride catalyzed by aurum-based catalyst of claim 1, characterized in that: the catalyst after grinding in step (3) should ensure that the surface is smooth, and then put into a blast drying oven at 90° C. for drying.

6. The method for acetylene hydrochlorination to vinyl chloride catalyzed by aurum-based catalyst of claim 5, further comprising:

(1) loading catalyst: padding a layer of quartz wool with a thickness of 10 mm on a middle position of a quartz reaction tube with a diameter of 10 mm, adding the catalyst into the reaction tube onto the layer of quartz wool, and then padding a layer of quartz wool with a thickness of 10 mm to cover the catalyst;

(2) before the reaction: purging the whole pipeline with $N_2$ at a flow rate of 20 mL min$^{-1}$ for 60 min, so as to remove air and moisture in the system; at the same time, increasing the temperature of the pipeline by 5° C./min to 150° C. and keeping for 30 min, and then increasing the temperature of the pipeline by 5° C./min to 180° C.; after that, introducing hydrogen chloride at a flow rate of 20 mL/min and keeping for 30 min, subsequently introducing both reaction gas at a flow rate of $V_{C2H2}$=16 mL/min and $V_{HCl}$=16.8 mL/min and keeping for 10 min, so as to ensure that the catalyst is in a gas atmosphere of acetylene and hydrogen chloride;

(3) after the reaction: first passing the gas phase product through an absorption flask containing NaOH solution to remove excess HCl and then analyzing online by gas chromatography GC-9790II to evaluate acetylene conversion and vinyl chloride selectivity.

* * * * *